United States Patent
Lipshitz et al.

(10) Patent No.: US 8,377,120 B2
(45) Date of Patent: Feb. 19, 2013

(54) INTRAOCCULAR IMPLANT SYSTEM WITH EXTERNAL LENS AND MIRRORS

(75) Inventors: Isaac Lipshitz, Herzliya Pituah (IL); Yariv Lipshitz, Ra'anana (IL)

(73) Assignee: Isaac Lipshitz, Herzliya Pituah (IL)

( * ) Notice: Subject to any disclaimer, the term of this patent is extended or adjusted under 35 U.S.C. 154(b) by 137 days.

(21) Appl. No.: 12/867,353

(22) PCT Filed: Feb. 19, 2009

(86) PCT No.: PCT/IL2009/000194
§ 371 (c)(1),
(2), (4) Date: Aug. 12, 2010

(87) PCT Pub. No.: WO2009/104186
PCT Pub. Date: Aug. 27, 2009

(65) Prior Publication Data
US 2011/0002464 A1 Jan. 6, 2011

Related U.S. Application Data

(60) Provisional application No. 61/066,388, filed on Feb. 19, 2008.

(51) Int. Cl.
*A61F 2/14* (2006.01)
*A61F 2/16* (2006.01)
(52) U.S. Cl. ...................... 623/5.11; 623/6.11; 623/6.35
(58) Field of Classification Search ............... 623/5.11, 623/5.12, 5.13, 6.11, 6.34, 6.35
See application file for complete search history.

(56) References Cited

U.S. PATENT DOCUMENTS

| 5,560,356 A | 10/1996 | Peyman |
| 2003/0014042 A1 | 1/2003 | Juhasz et al. |
| 2004/0236421 A1 | 11/2004 | Lipshitz et al. |
| 2005/0154457 A1 | 7/2005 | Aharoni et al. |

FOREIGN PATENT DOCUMENTS
WO 2007113832 A2 10/2007

OTHER PUBLICATIONS

International Search Report dated Jul. 13, 2009 in corresponding International Application No. PCT/IL2009/000194.
Written Opinion dated Jul. 13, 2009 in corresponding International Application No. PCT/IL2009/000194.

*Primary Examiner* — David Isabella
*Assistant Examiner* — Randy Shay
(74) *Attorney, Agent, or Firm* — Law Offices of Edward Langer (57) ABSTRACT

An intraocular implant adapted to be implanted within the interior of a human eye is disclosed. The aforesaid implant is selected from a group consisting of: an intracorneal implant, an anterior chamber implant, a sulcus implant, implant in the bag, posterior chamber implant and any combination thereof. The implant comprises means selected from a group consisting of reflective surfaces and electronic device. The implant is adapted to form at least one image of at least part of the field of vision on the retina. The image is selected of a group consisting of: artificial image and reflected image, and any combination thereof. The image is formed on the retina by a predetermined indirect path selected from (z) optical reflective path and (U) electronic processing. Optionally, also a refracted image may also be created on the retina.

4 Claims, 9 Drawing Sheets

INTRAOCCULAR IMPLANT SYSTEM WITH EXTERNAL LENS AND MIRRORS

FIELD OF THE INVENTION

This invention relates to an implant into the eye useful in improving vision in patients suffering from various retinal diseases and other eye diseases and eye conditions.

BACKGROUND OF THE INVENTION

This new disclosure is an improvement over U.S. Pat. No. 7,001,427 and US patent applications by Aharoni et al and US patent applications 2005005602, 200509691 and 20050154457 by Aharoni et al and U.S. Pat. No. 5,653,751 by Samiy et al. The current invention is different than U.S. Pat. No. 7,001,427 and US Patent applications 2005005602, 200509691 and 20050154457 since the above-mentioned patent and applications describe an implant that is always sealed within a capsule and is always located inside the bag of the natural lens and in the visual axis of light going into the eye. The apparatus described in the current invention may be located in other parts of the eye such as anterior chamber, inside the cornea or partly inside and partly outside the eye. Furthermore, it may include no sealed capsule or more than one sealed capsule, only part of the apparatus may be sealed and the sealed element may be located not in the visual axis. The apparatus in the current invention may also consist of more than one implant in more than one location in the eye, where each implant contains at least one electronic component.

The current invention also discloses the possibility to coat, not seal, at least some of the components using a biomaterial for safety reasons. Unlike the above patent and applications, the current invention does not necessarily require focusing optics as part of the implant and it allows the use of at least one electronic component external to the body as part of the apparatus. The current invention also allows for modifications and manipulations of the artificial image that is created on the retina, making it different than the natural image that is describes. Differences in illumination, colors, focus, contrast and magnification can be used to improve the patient's vision.

Further to the above, the current invention is also different than U.S. Pat. No. 5,653,751 by Samiy et al. That patent targets patients that have an opaque cornea. The image is captured external to the eye and then processed and transmitted into the eye using electronic means. Also, the above-mentioned patent discloses an apparatus, which is not implanted inside the eye and only a focusing element may be implanted. The current invention discloses a system where the image is first captured on an element that is located inside the eye. The current invention discloses an apparatus that is adapted to assist patients with retinal diseases and not corneal diseases as in the above patent. The current invention discloses an apparatus, which is implanted, comprising one or more implants, possibly with one or more electronic components placed outside the body. There are several existing patents and patent applications describing intracorneal implants. For examples see U.S. Pat. No. 7,455,691 (Feingold et al), U.S. Pat. No. 6,543,453 (Klima et al), U.S. Pat. No. 6,228,113 (Kaufman), U.S. Pat. No. 6,090,141 (Lindstrom), U.S. Pat. No. 5,699,141 (Monteil et al), U.S. Pat. No. 5,201,762 (Hauber), U.S. Pat. No. 5,123,921 (Werblin et al), U.S. Pat. No. 4,851,003 (Lindstrom), U.S. Pat. No. 4,799,931 (Lindstrom) and U.S. Pat. No. 4,470,159 (peyman). The current invention is different than all of these patents since it describes an intracorneal implant comprising either a reflective surface or at least one Component as part of an apparatus. None of these are mentioned in the above patents. There are several existing patents and patent applications describing anterior chamber implants. For example see U.S. Pat. No. 4,759,762 (Grendahl), U.S. Pat. No. 4,575,374 (Anis), U.S. Pat. No. 4,560,383 (Leiske), U.S. Pat. No. 4,168,547 (Konstantinov et al) and U.S. Pat. No. 4,551,864 (Akhavi). These patents deal with lenses that are implanted during cataract and refractive surgery, where the optical power is located in the optical path having a dioptric power. Entering light is refracted by those implants and passes through the pupil onto the retina. In the current invention the anterior chamber implant does not act as a simple refractive lens and not as an optical element in the center. It contains reflective surfaces and/or electronic elements. That light is reflected or reprocessed using other elements and only then an image is created onto the retina. U.S. Pat. No. 4,759,761 (Portnoy), U.S. Pat. No. 6,902,577 (Lipshitz et al), U.S. Pat. No. 6,920,399 (Lipshitz), U.S. Pat. No. 7,008,448 (Lipshitz et al) and PCT WO 2007/113832 A2 (Lipshitz et al) all disclose implants into the eye with reflective surfaces that are adapted to create a modified image on the retina, but they do not disclose an anterior chamber implant or an intracorneal implant that reflects light towards an external or contact lens.

SUMMARY OF THE INVENTION

It is hence one object of the invention to disclose an intraocular implant adapted to be implanted within the interior of a human eye selected from a group consisting of: intracorneal implant, anterior chamber implant, and any combination thereof. The implant comprises means selected from a group consisting of reflective surfaces and electronic device. The implant is adapted to form at least one image of at least part of the field of vision on the retina. The image is selected of a group consisting of: artificial image and reflected image, a refracted image and any combination thereof.

It is a core purpose of the invention to provide the image formed on the retina by a predetermined indirect path selected from (i) optical reflective path and (ii) electronic processing.

Another object of the invention is to disclose at least part of the implant at least partially adapted to provide protection of the eye from hazards being selected of a group consisting of: hazardous materials, hazardous radiation and heat. The protection is selected from a group consisting of: biocompatible material coating and, a sealed capsule and any combination thereof.

A further object of the invention is to disclose the implant is in communication with at least one external lens. The lens having at least one surface is at least partially reflective such that the image is created on the retina by a predetermined optical path comprising reflection from the implant towards the lens and then reflection from the lens towards the retina. The image is a magnified image adapted for treatment of the patient with a diseased retina.

A further object of the invention is to disclose the image created on the retina characterized by variable parameters selected of group consisting of magnification, brightness, color contrast, resolution, focus, prismatic effect and any combination thereof; further wherein said external component is optionally adapted to optimize said variable parameters.

A further object of the invention is to disclose the implant adapted to optionally form at least one refracted image on the retina.

A further object of the invention is to disclose an intraocular implant adapted to be implanted within the interior of a human eye selected from a group consisting of: posterior chamber implant, implant in the bag, sulcus implant and any combination thereof. The aforesaid implant comprises means selected from a group consisting of reflective surfaces and electronic device. The implant is adapted to form at least one image of at least part of the field of vision on the retina. The image is selected of a group consisting of: artificial image, reflected image, and any combination thereof. The image is formed on said retina by a predetermined indirect path selected from (i) optical reflective path and (ii) electronic processing.

A further object of the invention is to disclose an apparatus comprising: (a) at least one intraocular implant adapted to be implanted within the interior of a human eye selected from a group consisting of: Intracorneal implant, Anterior Chamber implant, sulcus implant, implant in the bag, posterior chamber implant and any combination thereof; the implant comprising means selected from a group consisting of reflective surfaces and electronic device; and (b) at least one external lens having at least one from a group consisting of a reflective surface and an electronic device. The apparatus is adapted to form at least one image of at least part of the field of vision on the retina. The image is selected of a group consisting of: artificial image, reflected image, refracted image and any combination thereof. The image is formed on the retina by a predetermined indirect path selected from (i) optical reflective path and (ii) electronic processing.

A further object of the invention is to disclose an apparatus comprising: (a) at least one intraocular implant adapted to be implanted within the interior of a human eye selected from a group consisting of: Intracorneal implant, Anterior Chamber implant, sulcus implant, implant I the bag, posterior chamber implant and any combination thereof; the implant comprising an electronic device; and (b) at least one external electronic component, in wireless communication with the implant. The implant is adapted to form at least one image of at least part of the field of vision on the retina. The image is selected of a group consisting of: artificial image and reflected image, refracted image and any combination thereof; wherein the image is formed on the retina by a predetermined indirect path selected from (i) optical reflective path and (ii) electronic processing.

A further object of the invention is to disclose at least part of the implant at least partially adapted to provide protection of the eye from hazards being selected of a group consisting of: hazardous materials, hazardous radiation and heat. The protection being selected from a group consisting of: biocompatible material coating and, a sealed capsule and any combination thereof.

A further object of the invention is to disclose the image characterized by variable parameters selected of the group consisting of: magnification, minification, prismatic effect, color contrast, illumination, focus, colors, and any combination thereof. The external component is optionally adapted to optimize the variable parameters.

A further object of the invention is to disclose a method for improving vision comprising steps of: (a) providing at least one intraocular implant; the implant comprising means selected from a group consisting of reflecting coating and electronic device; (b) implanting the at least one intraocular implant within the interior of a human eye at a location selected from a group consisting of the: the cornea, the Anterior Chamber, the sulcus, implant in the bag, posterior chamber implant and any combination thereof; and (c) forming at least one image of at least part of the field of vision on the retina; the image being selected of a group consisting of artificial image, reflected image, refracted image and any combination thereof; wherein the image is formed on the retina by a predetermined indirect path selected from (i) optical reflective path and (ii) electronic processing; the image formed on the retina is optionally characterized by variable parameters selected from magnification, brightness, color contrast, resolution, natural unchanged image and any combination thereof.

A further object of the invention is to disclose the step of forming an image of at least part of the field of vision on the retina additionally comprising step of providing an external lens. The lens has at least one of a group consisting of: reflective surface and electronic device. The step of forming the image on the retina is obtained by a predetermined optical path comprising paths selected from a group consisting of: (i) reflection from the implant towards the lens; (ii) reflection from the lens towards the retina, (iii) transmission from the implant towards the lens, (iv) transmission from the lens towards the retina.

A further object of the invention is to disclose an intraocular implant for use within the interior of a human eye selected from a group consisting of: Intracorneal implant, Anterior Chamber implant, the sulcus, implant in the bag, posterior chamber implant and any combination thereof; the implant comprising at least one reflective surface. The implant is adapted to form at least one image of at least part of the field of vision on the retina. The image is a reflected image, refracted image and any combination thereof. The image is formed on the retina by, a predetermined indirect reflective optical path. The implant is at least partially made from materials selected from a group consisting of shape memory materials, electroactive polymer, piezoelectric materials adapted to modify parameters selected from a group consisting of shape, curvature, transparency, optical properties, the optical slopes, image magnification, image location and any combination thereof by means selected from a group consisting of external radiation, heat, magnetic field, electrical field and any combination thereof.

A further object of the invention is to disclose an external lens having means selected from a group consisting of reflective surfaces and electronic device and any combination thereof. The lens is adapted to form an image of at least part of the field of vision on the retina. The image is received from at least one intraocular implant. The image formed on the retina is obtained by a predetermined optical path comprising paths selected from a group consisting of: (i) reflection from the implant towards the lens; (ii) reflection from the lens towards the retina, (iii) electronic transmission from the implant towards the lens, (iv) electronic transmission from the lens towards the retina, and any combination thereof.

A further object of the invention is to disclose a device adapted to create at least one recess in a person's cornea. The recess is adapted for implantation of at least one intracorneal implant. The implant comprises means selected of a group consisting of: reflective surface, electronic component and any combination thereof. The device uses at least one means of a group consisting of: laser, ultrasound, radio frequency, infrared, chemicals, mechanical element, and any combination thereof.

BRIEF DESCRIPTION OF THE EMBODIMENTS

In order to understand the invention and to see how it may be implemented in practice, preferred embodiments will now be described, by way of non-limiting example only, with reference to the accompanying drawings in which.

DETAILED DESCRIPTION OF THE PREFERRED EMBODIMENTS

The following description is provided, alongside all chapters of the present invention, so as to enable any person skilled in the art to make use of said invention and sets forth the best modes contemplated by the inventor for carrying our this invention. Various modifications, however, will remain apparent to those skilled in the art, since the generic principles of the present invention have been defined specifically to provide a means to improve the vision of patients suffering from retinal diseases, presbyopia and other eye diseases.

The terms "artificial vision" and "artificial image" refers hereinafter to vision/image that is created when at least one digitally created image is projected on the retina. This image artificially describes at least part of the scene seen by a person with normal vision, possibly with changes made to suite the needs of an individual patient suffering from a visual disorder. The at least one digitally created image, compared to a natural image, may be magnified, minified, unchanged in its size, have a prismatic effect, have stronger illumination, have weaker illumination, have different focus, have different colors (any color) from the object, have changing magnification, minification, focus, illumination and colors between different parts of the image, have a different contrast than the original/ natural image that the patient sees and any combination of the above. The artificial image may be adapted to focus for distance or for near for presbyopia persons. It may also be adapted to create depth perception and three-dimensional vision by processing the image either binocularly or monocularly.

The artificial image can be pre-customized according the person's needs and/or regulated and modified by the patient (as a non-limiting example: the patient may move it, make it brighter or magnify it). Changes to the artificial image can be made using any device adapted to regulate and make changes in the image. Said device may be connected to the image processing unit and/or connected to the electronic display either through mechanical/wire connection or through wireless connection.

The term "refracted image" refers hereinafter to an image that is refracted and reaches the retina unreflected and unprocessed by digital means.

The term "electronic component" refers hereinafter to at least one of the following: sensor/detector for capturing a full image or at least part of an image and/or scene, electronic display, an electronic circuit, microprocessor, image-processing unit, an image projector (light or electronic), means of receiving energy from an external source to the implant or generating energy inside the eye/implant (such as photoelectric cell or piezo electric as non-limiting examples), means of wire and/or wireless communications for broadcasting and receiving information (such as infrared and radio frequency as non-limiting examples), MEMS display scanning mirror micro or pico electro mechanical scanning mirror system and any combination of the above.

The term "anterior chamber implant" refers hereinafter to at least one anterior chamber implant, which is implanted inside the anterior chamber of the eye (the eye being either phakic, aphakic or pseudo-phakic). The at least one anterior chamber implant may have any shape, including, but not limited to: full or partial ring, circular, rounded, squared, elliptical, similar to a regular IOL with a central hole corresponding with the pupil and any combination of the above. It has at least one external surface, and may be implanted in any part of the anterior chamber. The anterior chamber implant may be coated, fully or partially, with a biomaterial such as Parylene (a trademark for a chemical vapor deposited poly(p-xylylene) polymer), ceramics, diamond-like carbon or glass, as non-limited examples, to prevent the eye from getting in contact with hazardous materials. The implant may fixate on the anterior chamber angle or on the iris The term "intracorneal implant" refers hereinafter to at least one intracorneal Implant, which implanted inside the cornea of the eye (the eye being either phakic, aphakic or pseudo-phakic). The at least one intra corneal implant may have any shape, including, but not limited to: full or partial ring, circular, rounded, squared, elliptical and any combination of the above. The intracorneal implant has at least one external surface. It may be implanted in any part of the cornea and may be coated, fully or partially, with a biomaterial such as Parylene (a trademark for a chemical vapor deposited poly(p-xylylene) polymer) or glass, as non-limited examples, to prevent the eye from getting in contact with hazardous materials. The term "implant in the bag" refers hereinafter to at least one eye implant, which is implanted in the lens capsule. The implant may have any shape, including, but not limited to: a ring, a partial ring, segmental, circular, linear, square, elliptical and any combination thereof. The implant is adapted to be implanted I a, aphakic or pseudophakic eye. It may be coated, fully or partially, with a biomaterial such as Parylene (a trademark for a chemical vapor deposited poly(p-xylylene) polymer) or glass, as non-limited examples, to prevent the eye from getting in contact with hazardous materials.

The term "electronic device" refers hereinafter to any device that is adapted to receive or detect at least part of a visual scene and create an artificial image that represents at least part of said scene on a person's retina. The aforesaid device contains at least one electronic component as defined above and, optionally, at least one optical component or an optical arrangement consisting of at least one: lens, mirror, diffractive optics element, fresnel, prism, adaptive optics element, holographic element and any combination of the above. The electronic device may use an internal source of energy, which is any source of energy generated internal to the body and/or contact lens such as piezo-electric source, photoelectric cell, a magnetic source or an electric generating material as non-limiting examples. It may also use an external source of energy, which is any source of energy generated external to the body such as an electromagnetic source, laser and infrared. The external source may be carried by the patient or attached to the patient's body/clothes and may be a mobile or non-mobile source. The electrical components in said device may communicate, transfer data and energy with each other using any wire or wireless means of communication.

The term "external lens" refers hereinafter to any lens or device that is placed external to the eye or on the eye such as a lens mounted on glasses or a contact lens.

The term "surface" refers hereinafter to a surface that may have any shape, including, but not limited to: spherical, aspheric, convex, concave, rounded, pointed, irregular, fixed shape, adjustable shape and any combination of the above. The surface may be external (anterior, posterior) or internal to the implant or external lens.

The term "recess" refers hereinafter to any tunnel opening, dissection, separation, niche, hole or any other opening inside the cornea in any shape that can host the intracorneal implant.

In the figures below where applicable: the cornea is 2, pupil is 4, the pupil opening is 6, entering light into the eye is 5, the zonules are 8, the lens capsule is 10, the retina is 12 and the macula is 14.

Figure 1:
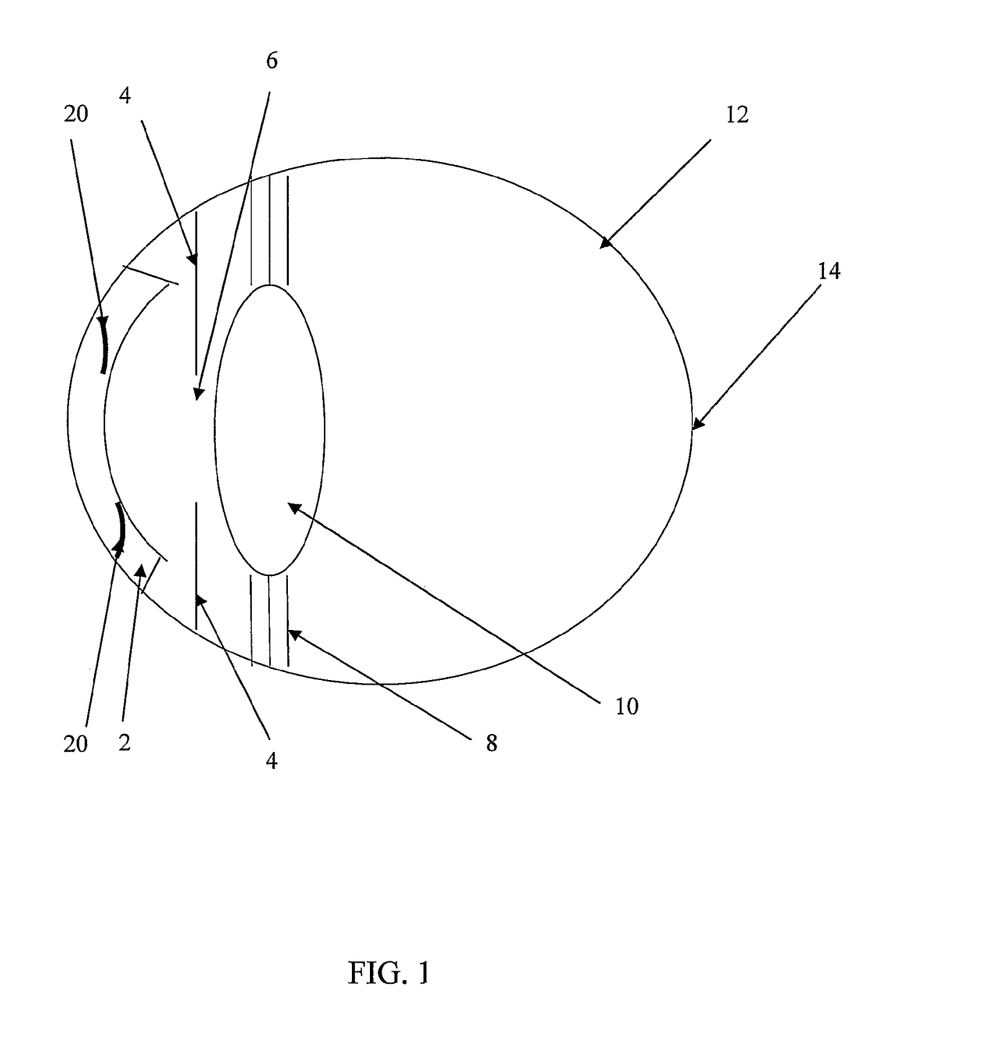
FIG. 1 presents a schematic illustration of an implanted intracorneal implant containing a reflective surface.

Reference is now made to FIG. 1 presenting a non-limiting example of an intracorneal implant 20 with reflective surfaces implanted inside cornea 2.

Figure 2:
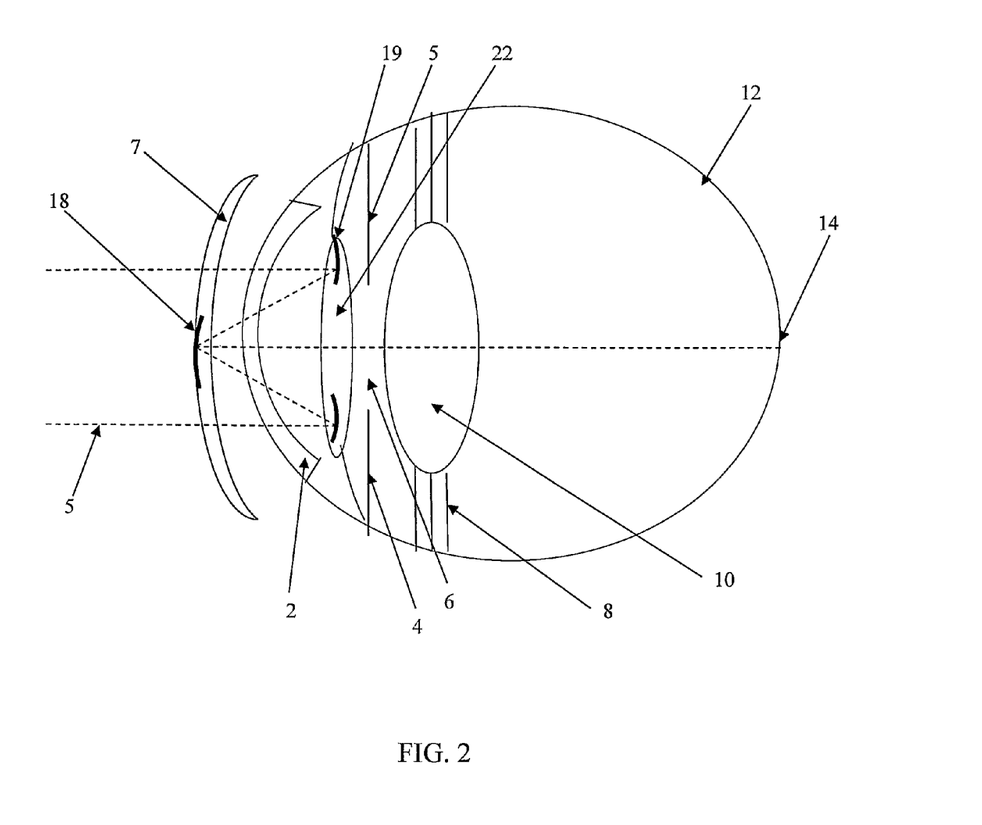
FIG. 2 presents a schematic illustration of an implanted anterior chamber implant containing a reflective surface and a reflective contact lens.

Reference is now made to FIG. 2 presenting a non-limiting example of an anterior chamber implant 22, which is implanted in the anterior chamber of an eye. In this non-limiting example the patient uses a contact lens 7 containing a reflective surface 18. Entering light 5 is at least partially reflected by anterior chamber reflective surface 19 towards contact lens reflective surface 18 and then reflected again towards retina 12. Reflective surfaces 18 and 19 are adapted to create a modified image 14 (in this example, a magnified image) on the macula of a patient suffering from a retinal disease such as Age-related Macular Degeneration or another eye condition.

Figure 3:
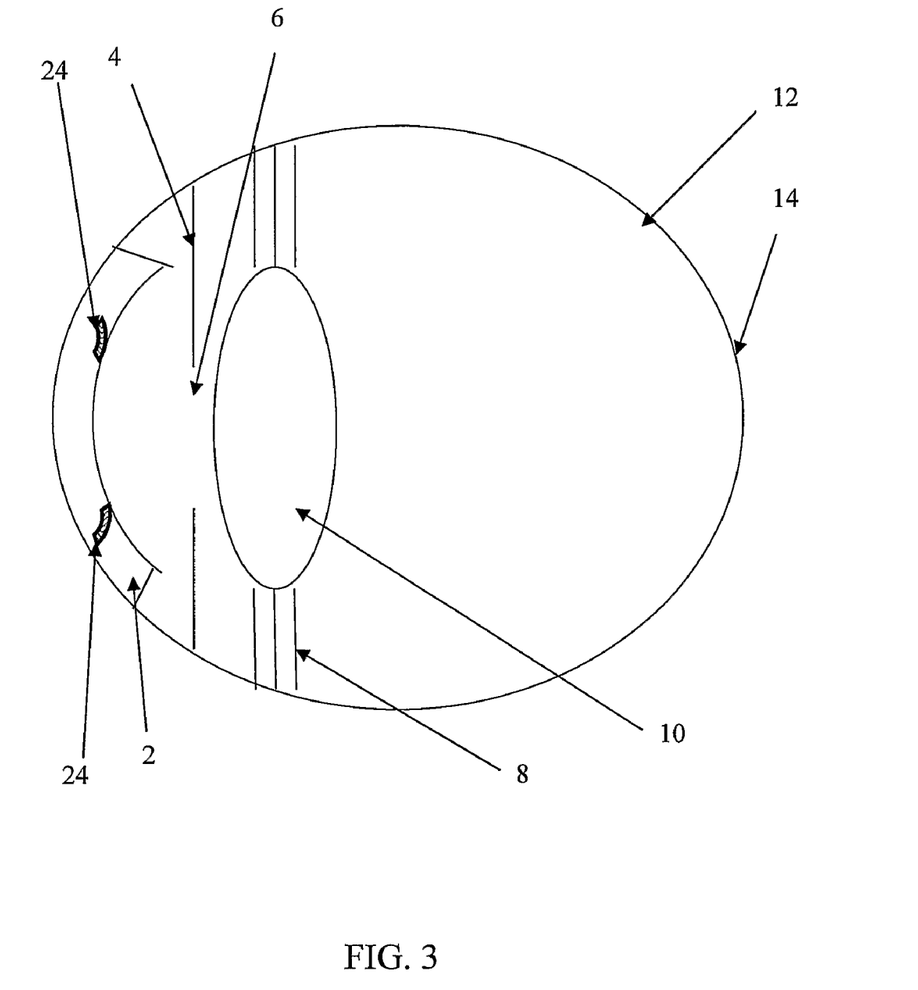
FIG. 3 presents a schematic illustration of an implanted intracorneal implant containing at least one electronic component.

Reference is now made to FIG. 3 presenting a non-limiting example of an apparatus containing an intracorneal implant 24, which is implanted inside cornea 2, containing electronic components (as defined above). The electronic components may communicate with each other using any means of wire or wireless communications and they may use energy generated from an internal or external source of energy.

Figure 4:
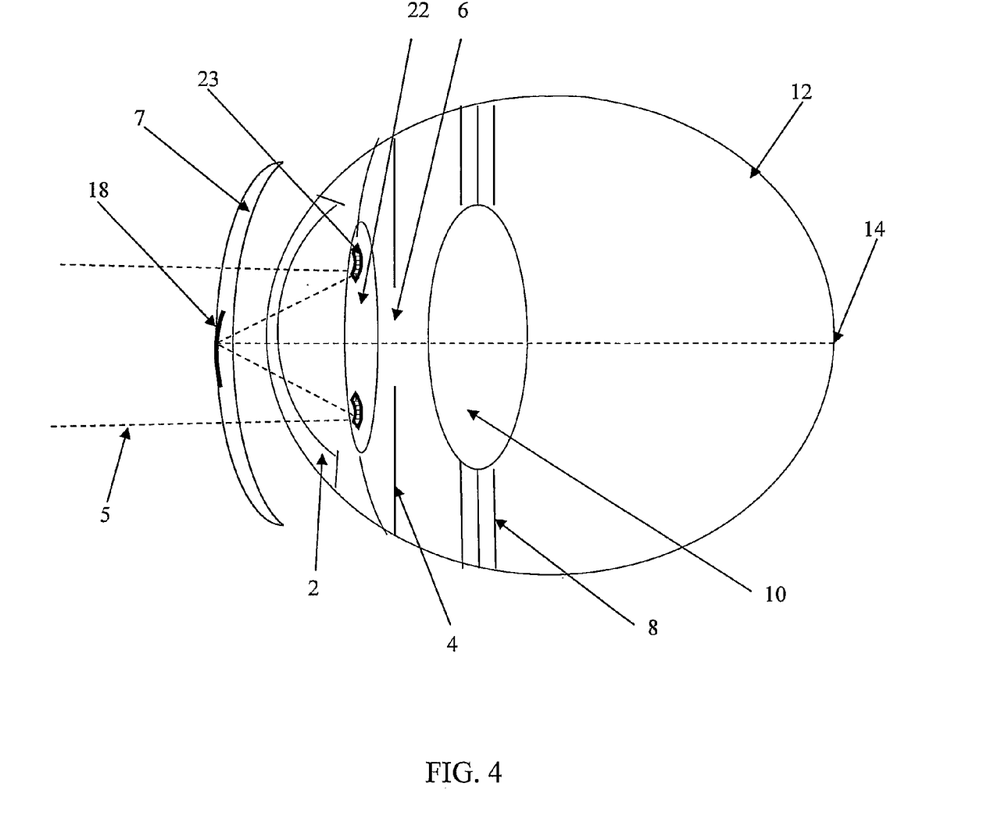
FIG. 4 presents a schematic illustration of an implanted anterior chamber implant containing at least one component and a reflective contact lens.

Reference is now made to FIG. 4 presenting a non-limiting example of an apparatus containing an anterior chamber implant 22, which is implanted in the anterior chamber of an eye. In this non-limiting example the patient uses a contact lens 7 containing a reflective surface 18. Anterior chamber implant 22 contains at least one electronic component 23 as defined above and is adapted to create an artificial image 14. It projects the image towards contact lens 7. The artificial image is then reflected by reflective surface 18 towards retina 12. Reflective surface 18 may magnify, minify or not change the image that is created on retina 12. At least part of electronic components 23 is placed out side the natural visual path, which is defined by pupil opening 6. The electronic components may communicate with each other using any means of wire or wireless communications and they may use energy generated from an internal or external source of energy.

Figure 5:
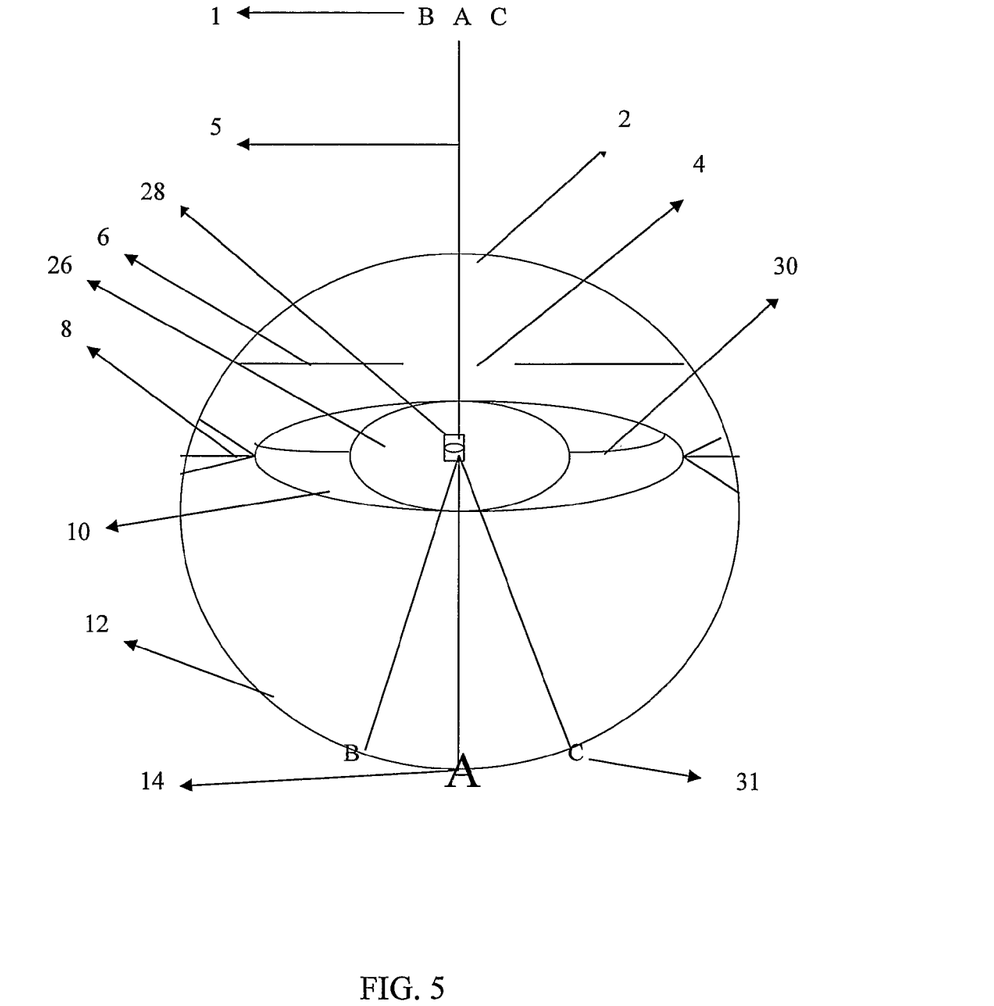
FIG. 5 presents a schematic illustration of an apparatus consisting of an intraocular implant with at least one component creating an artificial image, with perceived differences from the natural image.

Reference is now made to FIG. 5 presenting a non-limiting example of an electronic device 28 inside intraocular implant 26 with loops 30, which is implanted in lens capsule 10 and contains electronic components 28, as defined above. In this non-limiting example the components are concentrated in one area of intraocular implant 26, but not in a sealed capsule. At least some of the electronic components are coated with a biomaterial. The implant and the electronic components inside it are adapted to create an artificial image 14 that describes object 1 on the retina 12. In this non-limiting example the center of the image on retina 12 is magnified, while the rest of the image is unchanged. The electronic components may communicate with each other using any means of wire or wireless communications and they may use energy generated from an internal or external source of energy.

Figure 6:
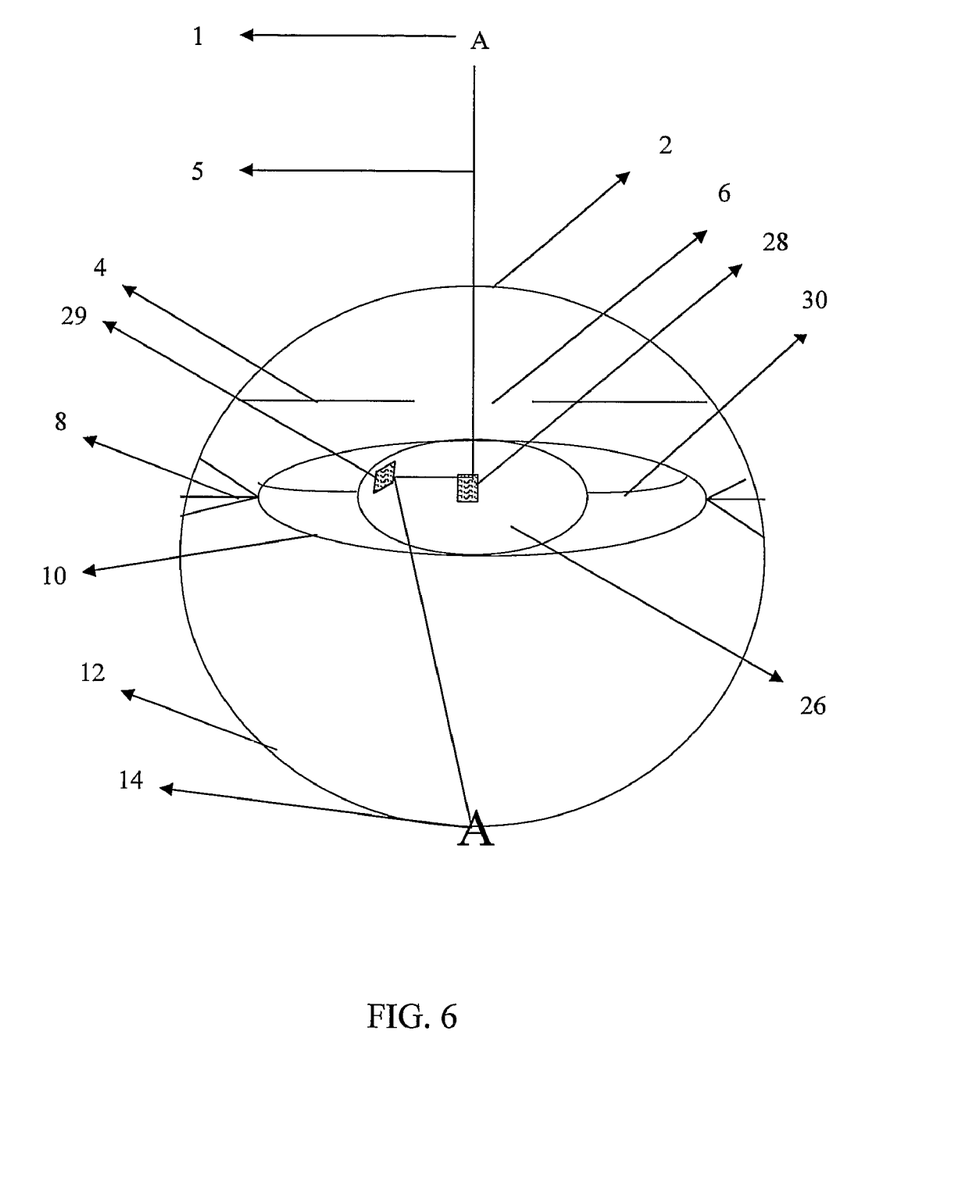
FIG. 6 presents a schematic illustration of an apparatus consisting of an intraocular implant containing more than one sealed capsule with at least one Component.

Reference is now made to FIG. 6 presenting a non-limiting example of an apparatus consisting of intraocular implant 26 with loops 30, which is implanted in the lens capsule 10 and contains part of an electronic device 28 located in the central part of implant 26, while part of the electronic device 29 is located at least partially in the peripheral part behind the iris. Parts 28 and/or 29 o the electronic device may be sealed in a capsule or at least partially coated with a biomaterial. Object 1 is projected as an artificial image 14 on retina 12.

Figure 7:
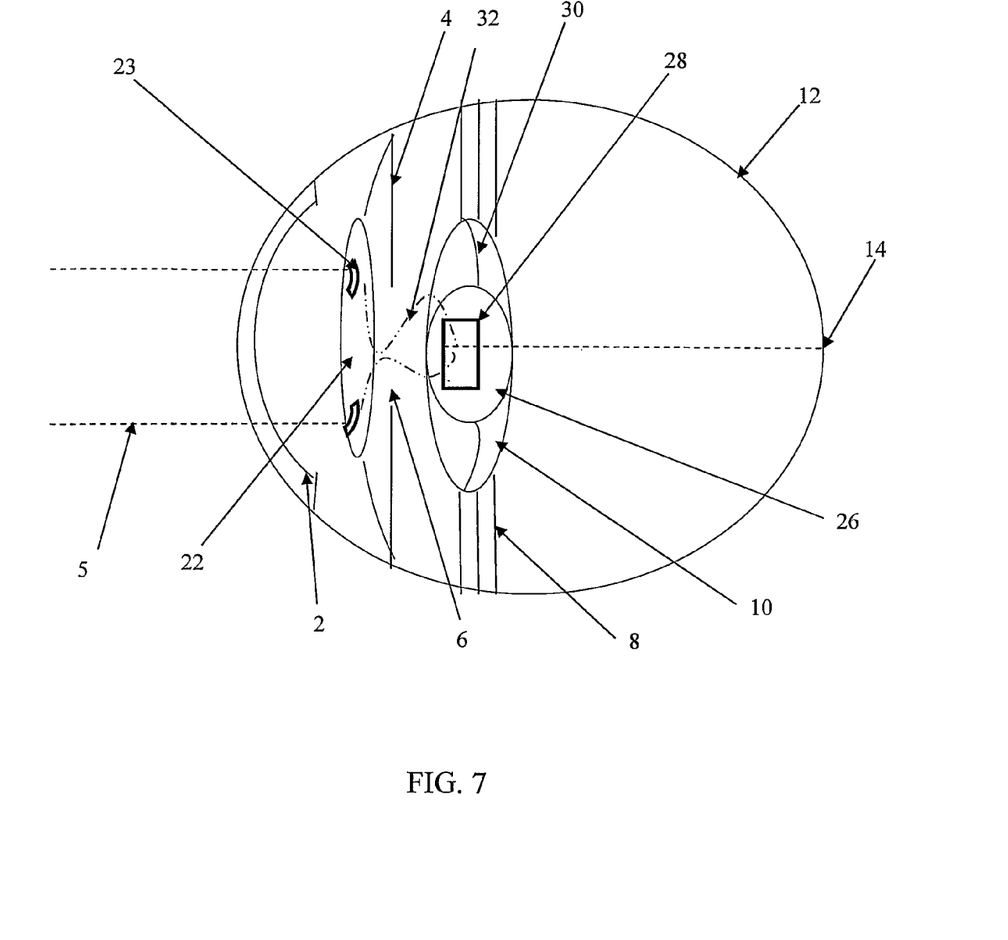
FIG. 7 presents a schematic illustration of an apparatus consisting of an anterior chamber implant and intraocular implant communicating via wireless means.

Reference is now made to FIG. 7 presenting a non-limiting example of an apparatus with an electronic device containing (1) an intraocular implant 26 with loops 30, which is implanted in lens capsule 10 and (2) an anterior chamber implant 22, which is implanted in the anterior chamber of the eye. In this non-limiting example, each of the implants contains at least one electronic component. The apparatus is adapted to create at least one artificial image 14 on retina 12. One part of electronic device 28 is in intraocular implant 26 and the other part 23 is in anterior chamber implant 22. Both parts may communicate between each other using any means of wire or wireless communications shown as 32. The same applies to the communication between the electronic components in each part of the device. The electronic components may use energy generated from any internal source inside the eye or any external source.

Figure 8:
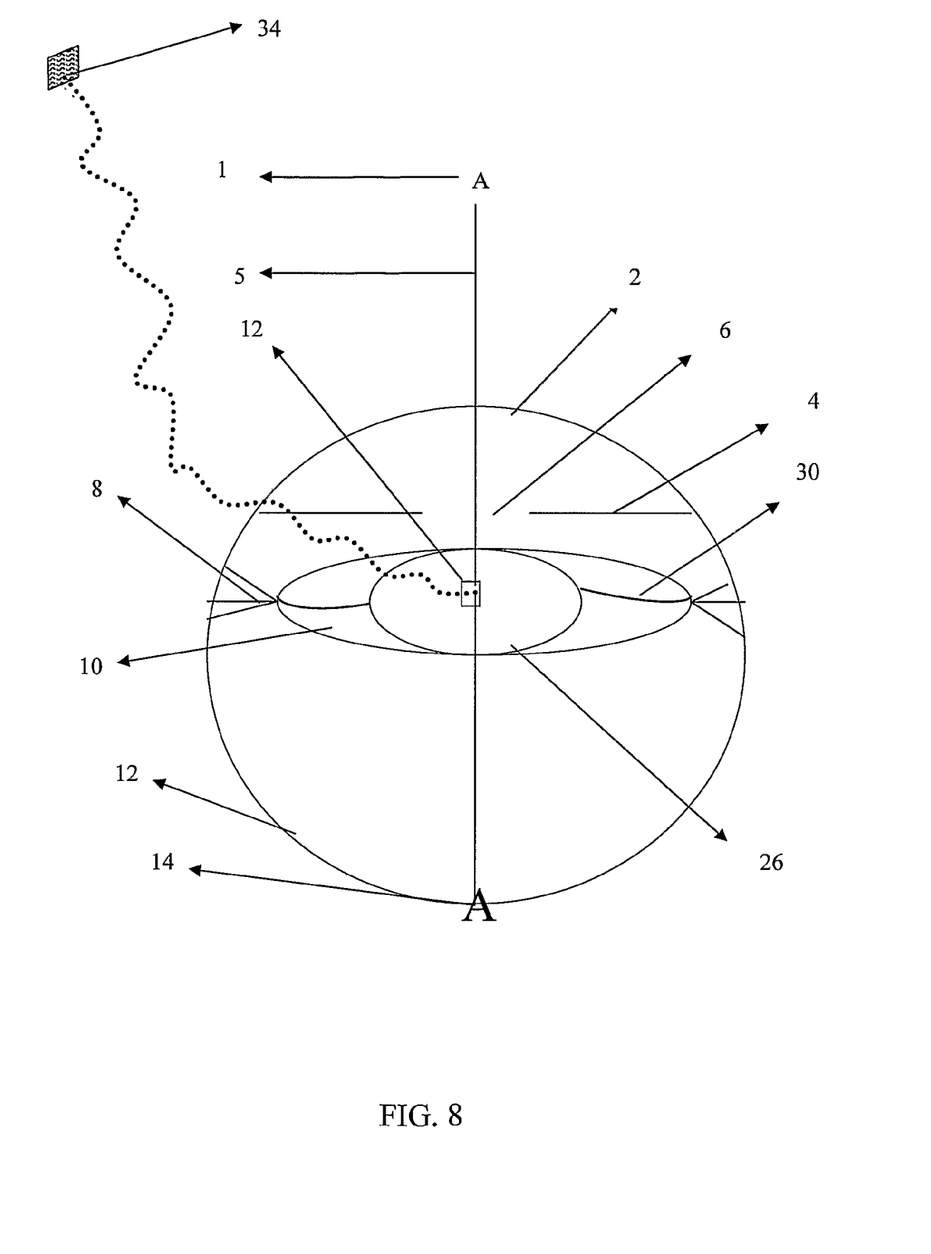
FIG. 8 presents a schematic illustration of an apparatus consisting of an intraocular implant with components communicating with an external data processing unit.

Reference is now made to FIG. 8 presenting a non-limiting example of an apparatus containing an electronic device located inside intraocular implant 26 with loops 30, which is implanted in lens capsule 10 and contains electronic components 28, as defined above and an external data processing unit 34. The apparatus is adapted to create an artificial image 14 on retina 12. In this non-limiting example the Components are concentrated in one area of intraocular implant 26 and they communicate with data processing unit 34 using wireless means of communication. The Components inside intraocular implant 26 may communicate with each other using any means of wire or wireless communications and they may use energy generated from an internal or external source of energy. Data processing unit 34 may be mobile and independent or contained in another device such as a watch or a cellular phone.

Figure 9:
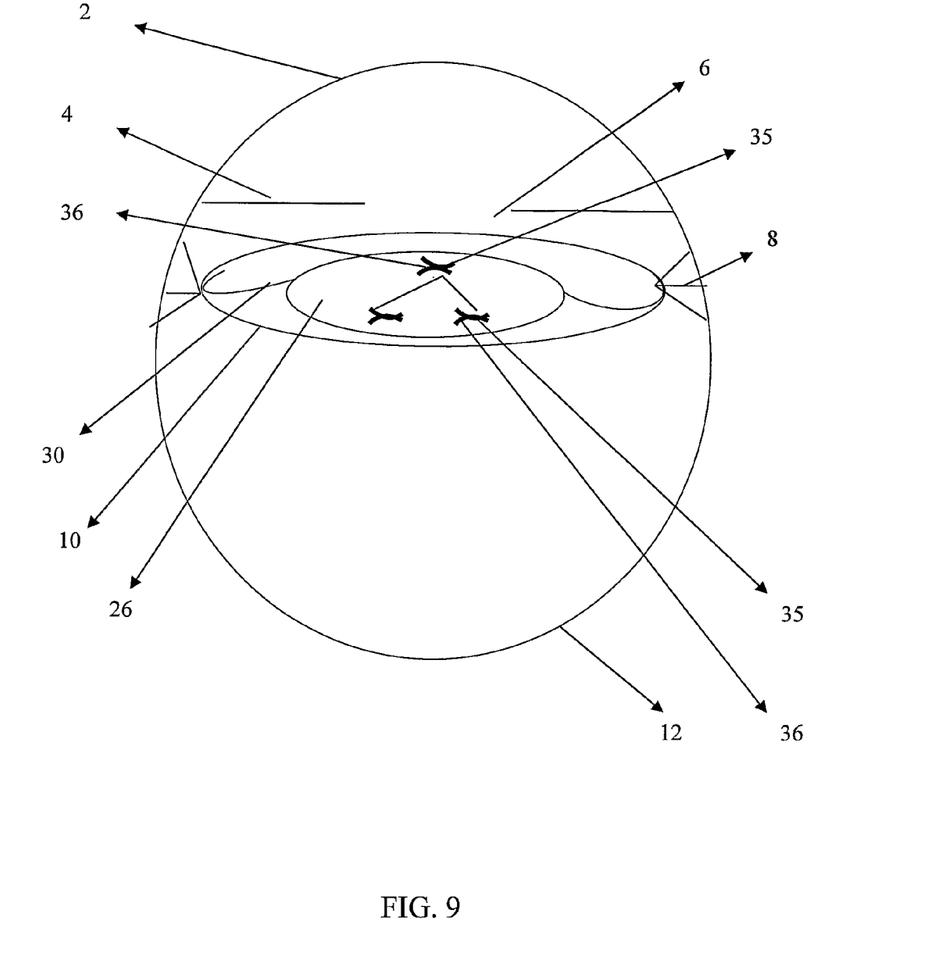
FIG. 9 presents a schematic illustration of an intraocular implant with reflective surfaces, whose shape and optical properties change when using external radiation.

Reference is now made to FIG. 9 presenting a non-limiting example of an apparatus containing intraocular implant 26 with loops 30, which is implanted in lens capsule 10 and contains reflective surfaces. Implant 26 is made of a material whose shape and/or optical properties are modified using external radiation such as electro-magnetic radiation. After lens 26 is implanted in the eye of a person, the initial positioning and shape of reflective surfaces 35 changes as a result of the external radiation to 36. The change in the mirror shape and positioning, may create magnification or change the magnification, minification, contrast, illumination and color seen on the retina 12 of a patient that suffers from an eye condition, as needed to improve his/her vision.

The invention claimed is:

1. An intraocular implant system adapted to be implanted within the interior of a human eye, said implant system comprising: an implant selected from a group consisting of: intracorneal implant, anterior chamber implant, and any combination thereof,
  said implant comprising reflective surfaces,
  and at least one external lens,
  said implant being in communication with said at least one external lens,
  said external lens having at least one surface being at least partially reflective,
  such that said implant and said external lens are adapted to form at least one reflected image of at least part of the field of vision on the retina,
  such that said image is created on said retina by a predetermined optical path comprising reflection from said implant towards said external lens and then reflection from said external lens towards the retina; said image being a magnified image adapted for treatment of a patient with a diseased retina.

2. The implant according to claim 1, wherein at least part of said implant is at least partially adapted to provide protection of the eye from hazards being selected of a group consisting of: hazardous materials, hazardous radiation and heat; said protection being selected from a group consisting of: biocompatible material coating and, a sealed capsule and any combination thereof.

3. The implant in claim 1, wherein said image created on said retina is characterized by variable parameters selected of group consisting of: magnification, brightness, color contrast, resolution, focus, prismatic effect and any combination thereof; further wherein said external component is optionally adapted to optimize said variable parameters.

4. The implant in claim 1, adapted to form at least one refracted image on said retina.

* * * * *